(12) United States Patent
Grundhofer

(10) Patent No.: US 9,636,286 B2
(45) Date of Patent: May 2, 2017

(54) ANTIMICROBIAL CLEANSER

(71) Applicant: Coloplast A/S, Humlebaek (DK)

(72) Inventor: Heather Grundhofer, Hugo, MN (US)

(73) Assignee: Coloplast A/S, Humlebaek (DK)

(*) Notice: Subject to any disclaimer, the term of this patent is extended or adjusted under 35 U.S.C. 154(b) by 0 days.

(21) Appl. No.: 14/299,422

(22) Filed: Jun. 9, 2014

(65) Prior Publication Data

US 2014/0378550 A1 Dec. 25, 2014

Related U.S. Application Data

(60) Provisional application No. 62/003,169, filed on May 27, 2014, provisional application No. 61/836,789, filed on Jun. 19, 2013.

(51) Int. Cl.

| | | |
|---|---|---|
| *A61K 8/41* | (2006.01) | |
| *A61K 8/37* | (2006.01) | |
| *A61K 8/55* | (2006.01) | |
| *A61K 8/60* | (2006.01) | |
| *A61K 8/73* | (2006.01) | |
| *A61K 8/86* | (2006.01) | |
| *A61Q 17/00* | (2006.01) | |
| *A61Q 19/10* | (2006.01) | |
| *C11D 1/62* | (2006.01) | |
| *C11D 1/66* | (2006.01) | |
| *C11D 1/75* | (2006.01) | |
| *C11D 1/88* | (2006.01) | |
| *C11D 1/94* | (2006.01) | |
| *C11D 3/22* | (2006.01) | |
| *C11D 3/37* | (2006.01) | |
| *C11D 3/48* | (2006.01) | |

(52) U.S. Cl.
CPC .............. *A61K 8/416* (2013.01); *A61K 8/375* (2013.01); *A61K 8/418* (2013.01); *A61K 8/553* (2013.01); *A61K 8/602* (2013.01); *A61K 8/604* (2013.01); *A61K 8/737* (2013.01); *A61K 8/86* (2013.01); *A61Q 17/005* (2013.01); *A61Q 19/10* (2013.01); *C11D 1/94* (2013.01); *C11D 3/225* (2013.01); *C11D 3/227* (2013.01); *C11D 3/3776* (2013.01); *C11D 3/48* (2013.01); *A61K 2800/48* (2013.01); *A61K 2800/74* (2013.01); *A61K 2800/75* (2013.01); *C11D 1/62* (2013.01); *C11D 1/66* (2013.01); *C11D 1/75* (2013.01); *C11D 1/886* (2013.01)

(58) Field of Classification Search
CPC ........ A61K 8/375; A61K 8/416; A61K 8/553; A61K 8/602; A61K 8/604; A61K 8/737; A61K 8/86; A61K 2800/74; A61K 2800/75; A61K 2800/48; A61Q 19/10; A61Q 17/005; C11D 1/62; C11D 1/66; C11D 1/75; C11D 1/94; C11D 1/886; C11D 3/225; C11D 3/227; C11D 3/3776; C11D 3/48

See application file for complete search history.

(56) References Cited

U.S. PATENT DOCUMENTS

| | | | | |
|---|---|---|---|---|
| 3,855,140 | A | * 12/1974 | Billany et al. | ................. 510/132 |
| 4,209,449 | A | 6/1980 | Mayhew et al. | |
| 5,635,462 | A | * 6/1997 | Fendler et al. | ................. 510/131 |
| 5,683,683 | A | 11/1997 | Scafidi | |
| 5,719,113 | A | * 2/1998 | Fendler et al. | ................. 510/382 |
| 5,869,071 | A | * 2/1999 | Wieselman | .............. A61K 8/31 |
| | | | | 424/401 |
| 8,293,802 | B2 | * 10/2012 | Modak | ................... A61K 8/042 |
| | | | | 514/722 |
| 8,349,363 | B2 | 1/2013 | Huang et al. | |
| 8,367,568 | B2 | 2/2013 | Bradley et al. | |
| 2003/0022941 | A1 | * 1/2003 | Taylor | .................... A01N 25/16 |
| | | | | 514/642 |
| 2003/0053961 | A1 | * 3/2003 | Eccard | ............................ 424/47 |
| 2007/0184016 | A1 | * 8/2007 | Macinga | ................ A01N 33/12 |
| | | | | 424/78.27 |
| 2011/0144214 | A1 | 6/2011 | Snyder et al. | |

(Continued)

FOREIGN PATENT DOCUMENTS

| | | |
|---|---|---|
| GB | 2326167 | 12/1998 |
| WO | 9531962 | 11/1995 |

(Continued)

OTHER PUBLICATIONS

Abbas, "Handbook of Detergents, Part E: Applications", Surfactant Science Series, vol. 141, Chapter 7, "Body-Cleansing Technology", 2009, pp. 135-150.

Bernhofer, et al., Development of an in vitro Model for the Prediction of Skin Irritation Potential, Johnson & Johnson Consumer Products Worldwide, Presented at 1997 Congress on in Vitro Biology, Washington, D.C., 1997, 4 pages.

Faller, et al., "Predictive Ability of Reconstructed Human Epidermis Equivalents for Assessment of Skin Irritation of Cosmetics", Toxicology in Vitro, 16(5), pp. 557-572, 2002.

(Continued)

*Primary Examiner* — John Pak
*Assistant Examiner* — Nathan W Schlientz
(74) *Attorney, Agent, or Firm* — Coloplast Corp., Coloplast A/S; Nick Baumann

(57) ABSTRACT

Compositions containing a quaternary ammonium compound (QAC) "active" to provide an antimicrobial property, a quaternized phospholipid which provides a reduction in potential irritancy of other ingredients as well as foaming and cleansing properties, a second non-ionic or amphoteric surfactant (such as an alkyl amine oxide or linear alkyl polyglucoside) to provide increased foam volume and cleansing properties, a non-ionic or quaternized polymer (such as hydroxypropylmethylcellulose or hydroxypropyl guar hydroxypropyl trimonium chloride) which can provide thickening, foam structure and improved after-feel properties are described.

13 Claims, 7 Drawing Sheets

(56) References Cited

U.S. PATENT DOCUMENTS

2012/0070341 A1  3/2012  Eder et al.
2013/0035396 A1  2/2013  Moen et al.

FOREIGN PATENT DOCUMENTS

WO    0123517    4/2001
WO    02076207   10/2002

OTHER PUBLICATIONS

Hall, et al., "Comparisons of in Vitro and in Vivo Skin Responses to Surfactants with a Range of Irritancy Potential", The Procter & Gamble Company, Human Safety Department, Cincinnati, OH; Presented at "International Symposium on Irritant Contact Dermatitis," Zurich, Switzerland, Poster #44P, Apr. 1994, 4 pages.

Kandarova, et al., "In Vitro Skin Irritation Test: Increasing the Sensitivity of the EpiDerm Skin Irritation Protocol Evaluated in the ECVAM Skin Irritation Validation Study", Mattek Corporation, Ashland, MD., ATLA, No. 37, 2009, pp. 671-689.

* cited by examiner

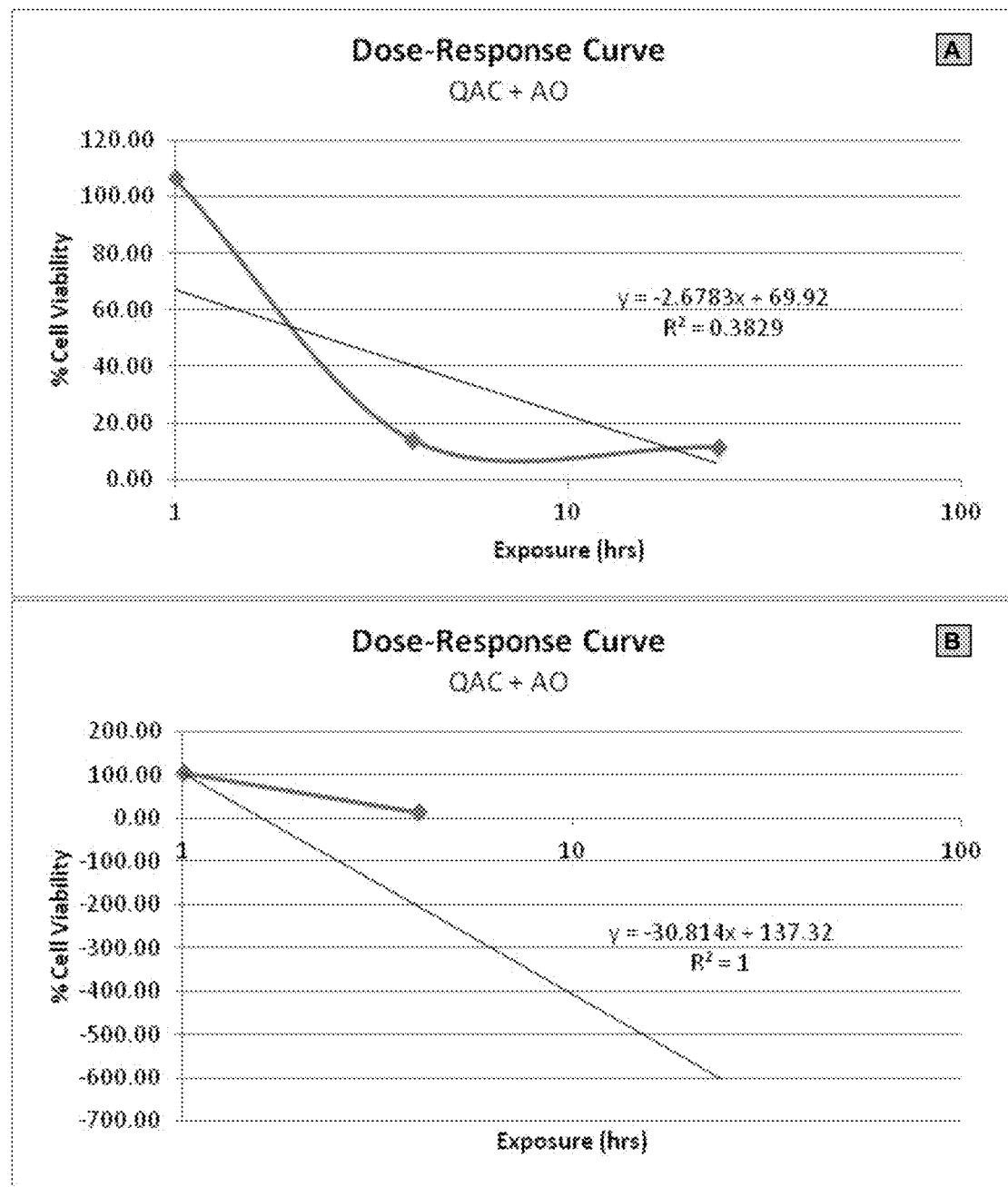
FIG. 1. Dose-Response Curves of Sample 1.

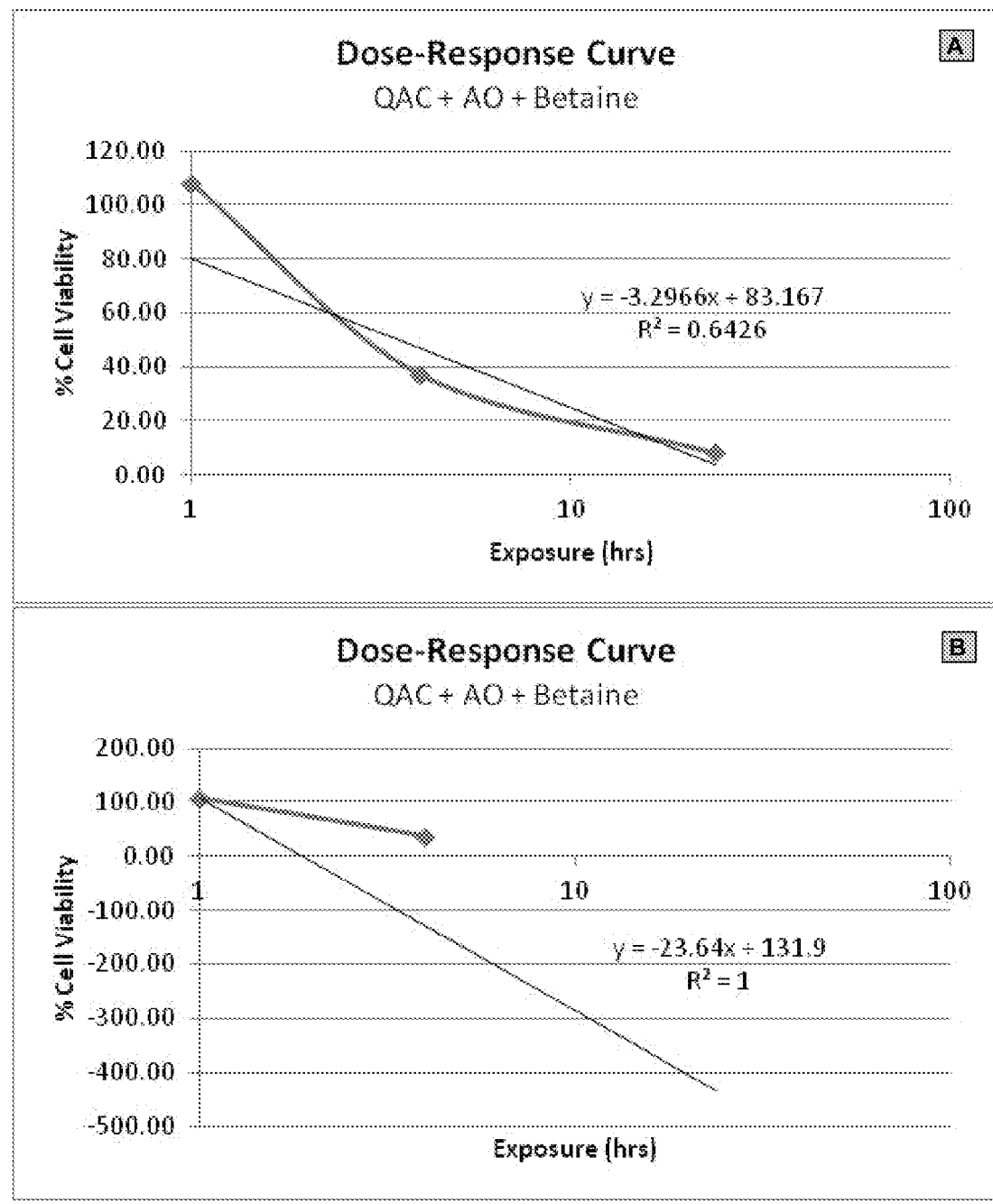
FIG. 2. Dose-Response Curves of Sample 2.

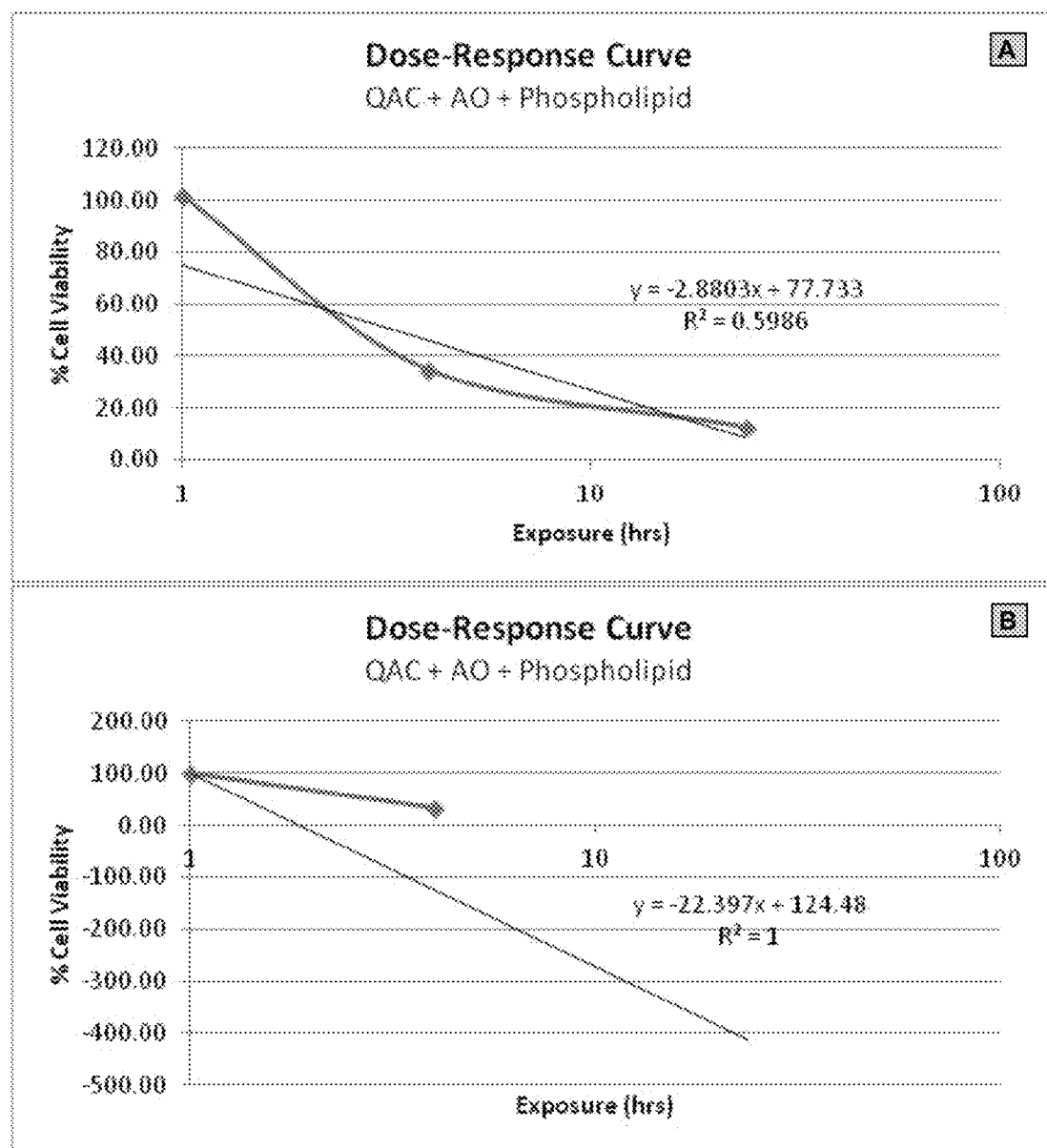
FIG. 3. Dose-Response Curves of Sample 3.

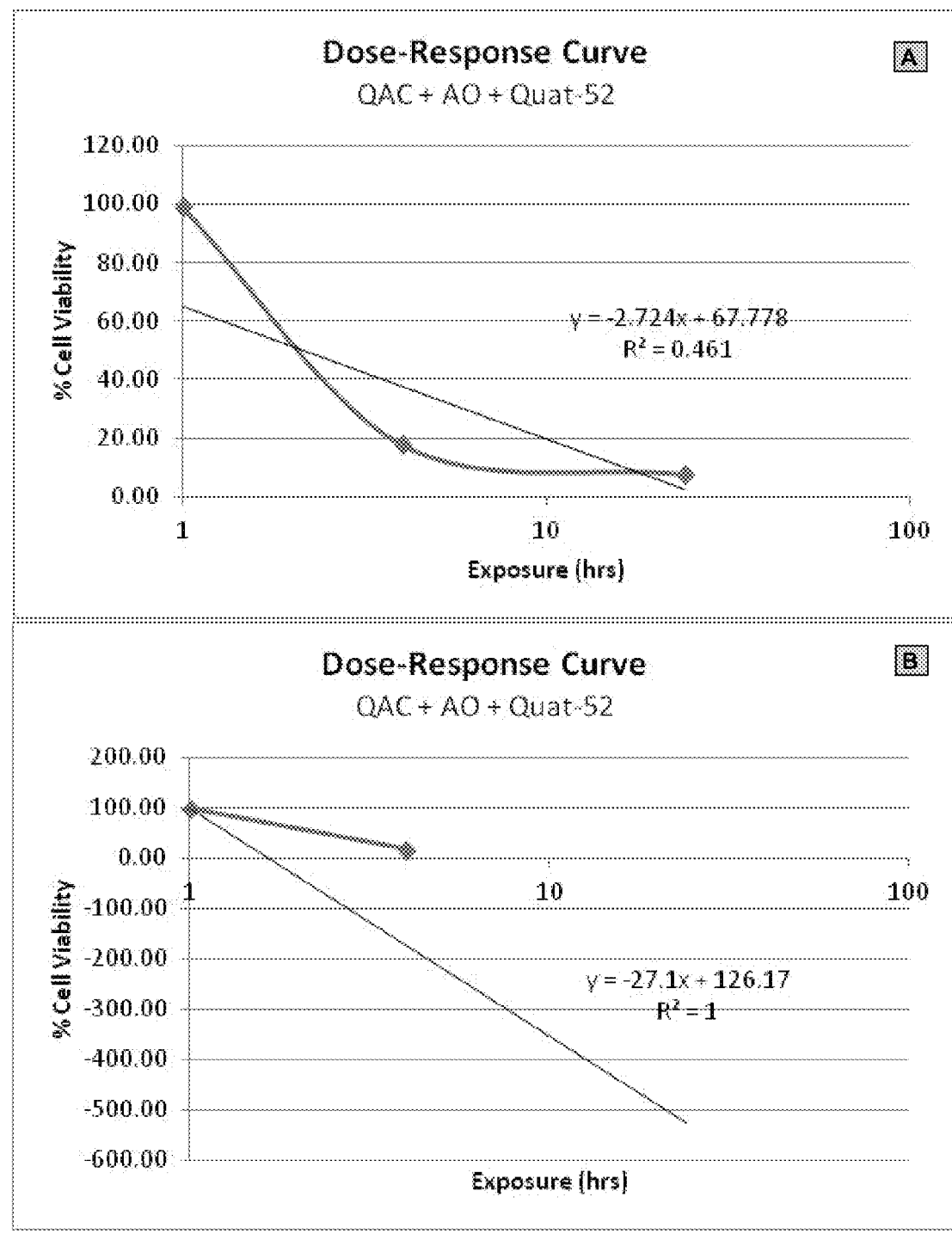
FIG. 4. Dose-Response Curves of Sample 7.

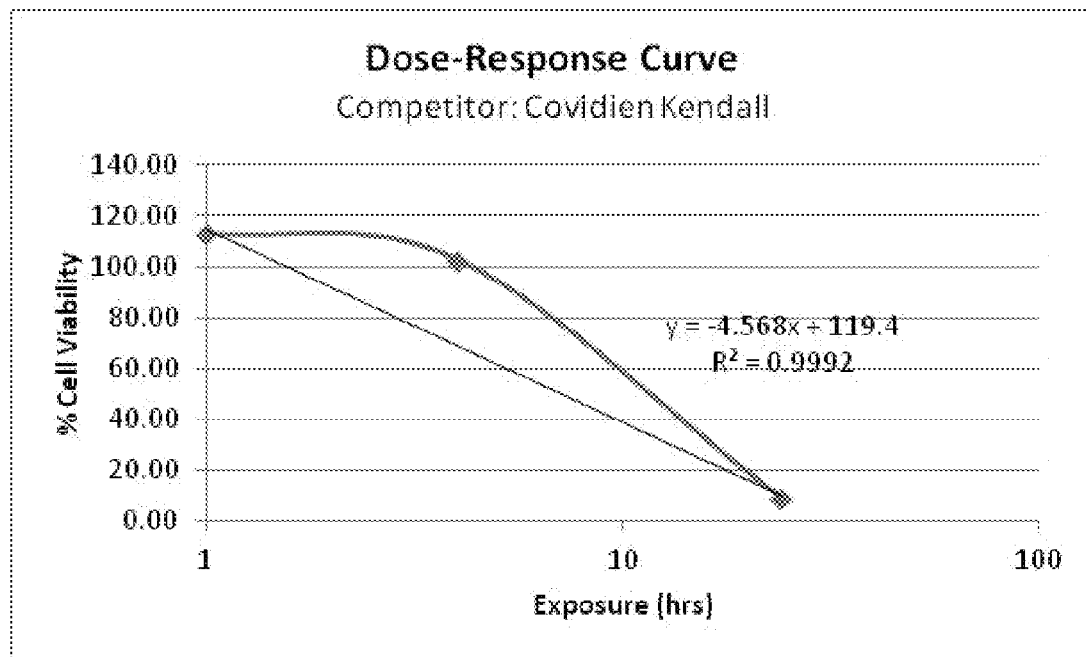
FIG. 5. Dose-Response Curve of Sample 4.
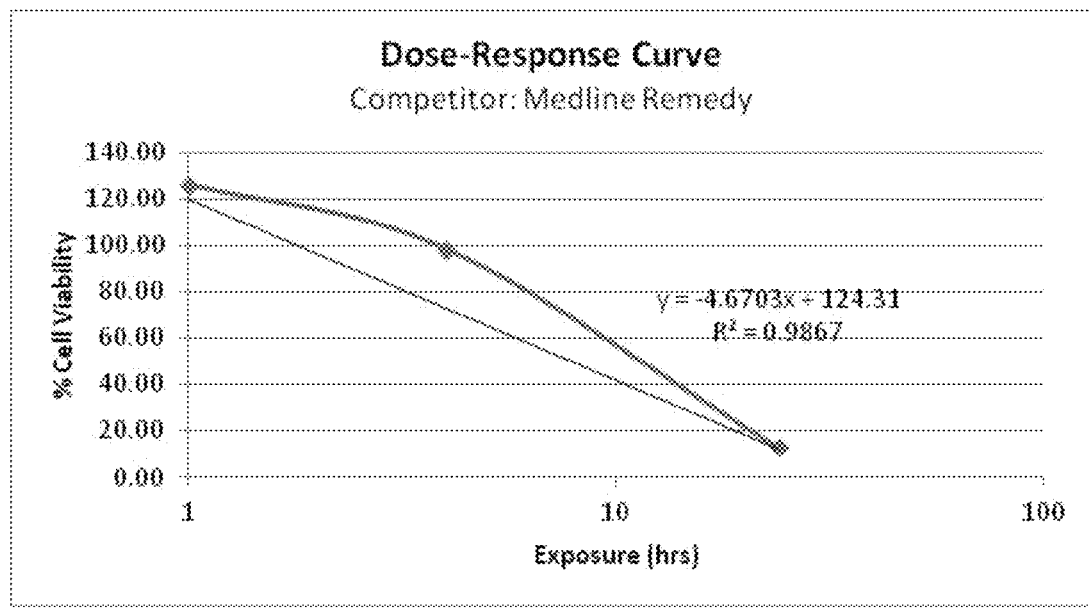
FIG. 6. Dose-Response Curve of Sample 5.

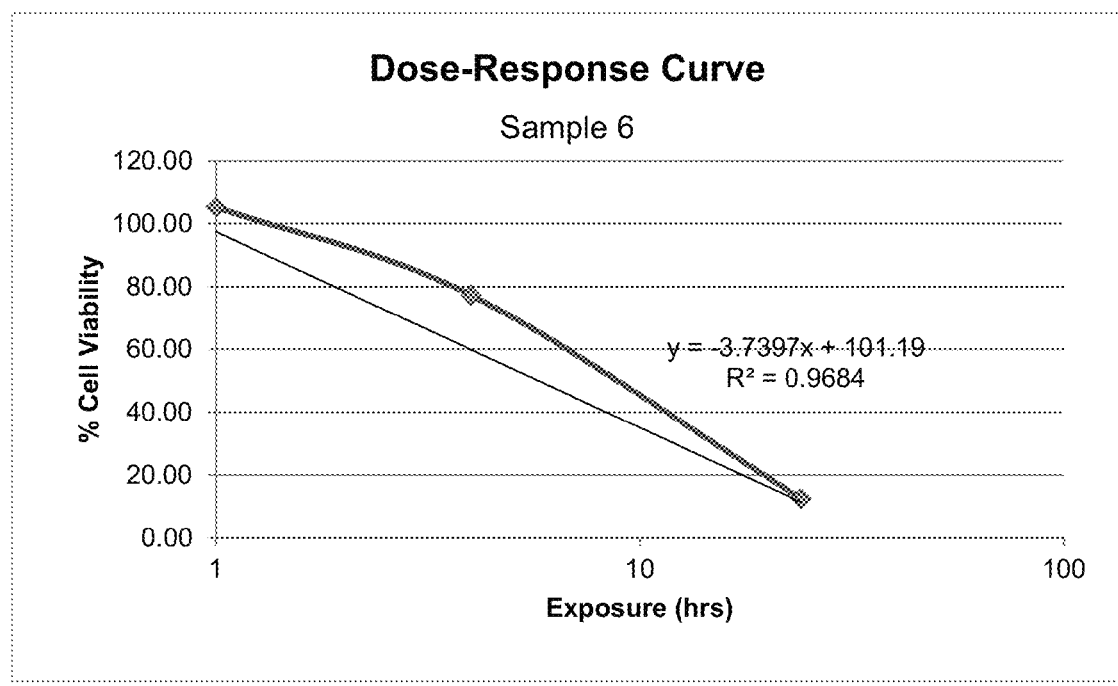
FIG. 7. Dose-Response Curve of Sample 6.

ANTIMICROBIAL CLEANSER

CROSS REFERENCE TO RELATED APPLICATIONS

This application claims the benefit of Provisional Application Ser. No. 62/003,169, filed May 27, 2014, and claims the benefit of Provisional Application Ser. No. 61/836,789, filed Jun. 19, 2013, the contents of which are incorporated herein in their entirety for all purposes.

TECHNICAL FIELD

The invention relates generally to compositions that include a quaternary ammonium compound; a first surfactant, comprising a quaternized phospholipid; a second surfactant, comprising a nonionic surfactant or amphoteric surfactant; and a nonionic polymer or a quaternized polymer.

BACKGROUND

There continues to be a demand for gentle, efficacious, and effective antimicrobial compositions that are mild, cost effective and preferably soothing to the skin. Many antimicrobial compositions are in the market place, however, many have one or more disadvantages in terms of effectiveness, skin irritation, skin dried and/or cracked and/or other disadvantages. These can that are not pleasing to the consumer due to lack or foam or feel.

Currently, Triclosan and Triclocarban, are the major antimicrobial active ingredients in the skin cleansing market. Triclosan and Triclocarban have become disfavored as antimicrobial agents by some consumers. Consumers are seeking alternatives to these active ingredients and yet desire effective cleansing compositions.

Therefore, a need exists for a cleansing composition that overcomes one or more of the current disadvantages noted above.

BRIEF SUMMARY OF THE EMBODIMENTS

The present embodiments surprisingly provide a mild, efficacious antimicrobial formulation for use in dermal cleansing in either rinse-off or leave-on applications. The antimicrobial formulation includes a quaternary ammonium compound (QAC) "active" to provide an antimicrobial property, a first surfactant as a quaternized phospholipid which provides a reduction in potential irritancy of other ingredients as well as foaming and cleansing properties, a second non-ionic or amphoteric surfactant (such as an alkyl amine oxide or linear alkyl polyglucoside) that provides an increased cleansing property and a non-ionic polymer or quaternized polymer (such as hydroxypropyl methylcellulose or hydroxypropyl guar hydroxypropyl trimonium chloride) which can provide thickening, foam structure and after-feel properties.

To further improve the mildness of the formulations, skin adjuvants can be included which do not inhibit the antimicrobial effectiveness of the formulations. The adjuvants include, for example, glycerol and its ester derivatives (such as polyglyceryl-4 caprate), ethoxylated esters such as (PEG-7 glyceryl cocoate or glycereth-18 ethylhexanoate (and) glycereth-18), urea, and/or ethoxylated glucose derivatives (such as methyl gluceth-10 and methyl gluceth-20). The formulations may also contain other functional ingredients such as dyes, fragrances, pH adjusters, chelating agents, etc.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIG. 1 depicts dose-response curves A and B of Sample 1 in Example 2.

FIG. 2 depicts dose-response curves A and B of Sample 2 in Example 2.

FIG. 3 depicts dose-response curves A and B of Sample 3 in Example 2.

FIG. 4 depicts dose-response curves A and B of Sample 7 in Example 2.

FIG. 5 depicts a dose-response curve of Sample 4 in Example 2.

FIG. 6 depicts a dose-response curve of Sample 5 in Example 2.

FIG. 7 depicts a dose-response curve of Sample 6 in Example 2.

DETAILED DESCRIPTION

Figure 8:
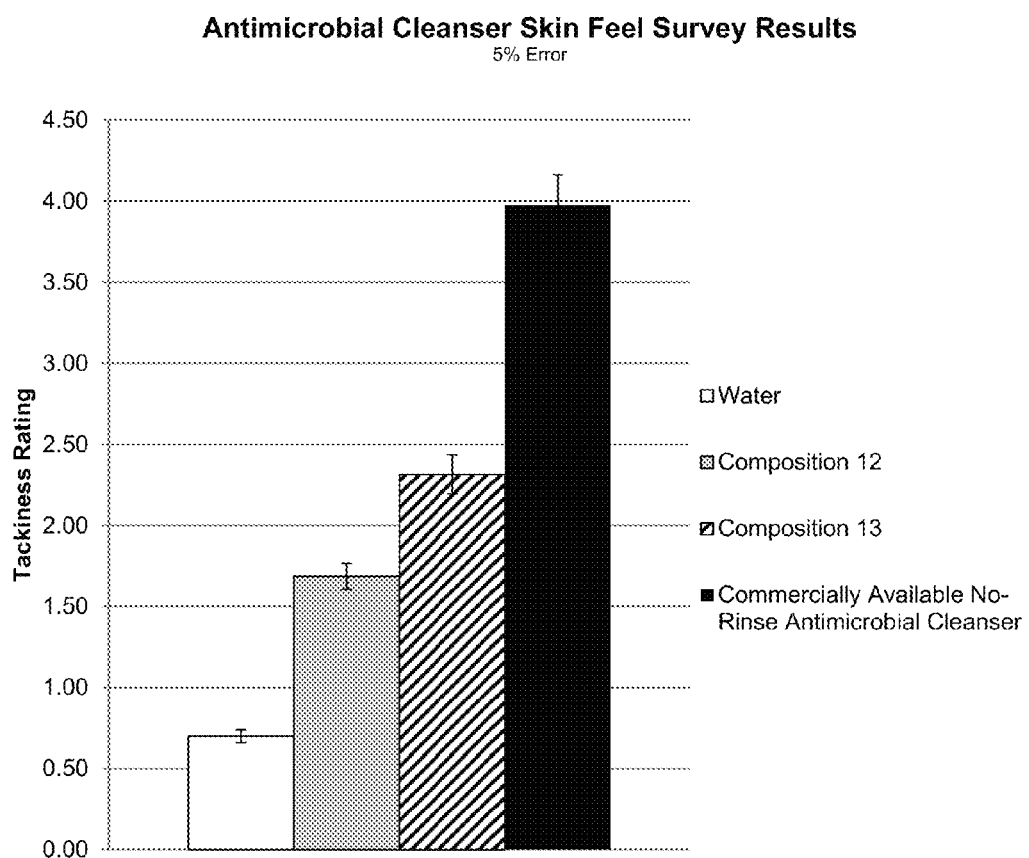
FIG. 8 depicts a survey for antimicrobial cleansers skin feel results.

In the specification and in the claims, the terms "including" and "comprising" are open-ended terms and should be interpreted to mean "including, but not limited to . . . " These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

In one embodiment, a composition that includes a quaternary ammonium compound; a first surfactant, comprising a quaternized phospholipid; a second surfactant, comprising a nonionic surfactant or amphoteric surfactant; and a nonionic polymer or a quaternized polymer is provided.

The formulae provide herein are mild, efficacious antimicrobial formulations for use in dermal cleansing in either rinse-off or leave-on applications. They are composed of a quaternary ammonium compound (QAC) "active" to provide an antimicrobial property, a quaternized phospholipid which provides a reduction in potential irritancy of other ingredients as well as foaming and cleansing properties, a second non-ionic or amphoteric surfactant (such as an alkyl amine oxide or linear alkyl polyglucoside) to provide increased foam volume and cleansing properties, a non-ionic or quaternized polymer (such as hydroxypropylmethylcellulose or hydroxypropyl guar hydroxypropyl trimonium chloride) which can provide thickening, foam structure and improved after-feel properties.

To further improve the mildness of the formulation, skin adjuvants can be included which do not inhibit the antimicrobial effectiveness of the formulations. These include: glycerol and its ester derivatives (such as polyglyceryl-4 caprate), ethoxylated esters such as (PEG-7 Glyceryl Cocoate or Glycereth-18 Ethylhexanoate (and) Glycereth-18), urea, ethoxylated glucose derivatives (such as methyl gluceth-10 and methyl gluceth-20). The formulations may also contain other functional ingredients such as dyes, fragrances, pH adjusters, chelating agents, etc.

Most QAC active antimicrobials fall into one of two categories, i) they do not show antimicrobial efficacy or, ii) they are very irritating to dermal cells. The formulae herein combine both an efficacious antimicrobial property with a mild, aesthetically pleasing property as evidenced by an in vitro whole toxicology assay and consumer panel results noted in the Example section below.

The compositions described herein can include one or more of the materials described in the following paragraphs.

Quaternary ammonium compounds (QAC) are antimicrobial agents useful herein. The cationic or cationically-active substances are based on nitrogen centered cationic moieties with a net positive change.

Suitable quaternary ammonium compounds have the general formula:

$$N^+R^1R^2R^3R^4X^-$$

wherein $R^1$, $R^2$, $R^3$ and $R^4$, independently of each other, are alkyl groups, aliphatic groups, aromatic groups, alkoxy groups, polyoxyalkylene groups, alkylamido groups, hydroxyalkyl groups, aryl groups, each with from 1 to 22 carbon atoms or $H^+$ ions; and $X^-$ represents a halogen, acetate, phosphate, nitrate or alkyl sulfate.

Optionally, any anion can be used in the quaternary salt. The anion may be organic or inorganic with proviso that the material is cosmetically acceptable. Typical inorganic anions are halides, sulfates, phosphates, nitrates and borates. Organic anionic counter ions include methosulfate, toluoyl sulfate, acetate, citrate, tartrate, lactate, gluconate, and benzenesulfonate.

Particular cationic active ingredients include, for example, but are not limited to, alkyl dimethyl benzyl ammonium chloride (ADBAC), alkyl dimethyl ethylbenzyl ammonium chloride, dialkyl dimethyl ammonium chloride, benzethonium chloride, N,N-bis-(3-aminopropyl) dodecylamine, chlorhexidine gluconate, PHMB (polyhexamethylene biguanide), salt of a biguanide, a substituted biguanide derivative, an organic salt of a quaternary ammonium containing compound or an inorganic salt of a quaternary ammonium containing compound or mixtures thereof.

The active ingredient can also include low viscosity derivatives of tetracalcium phosphate (TTCP) type fillers and bis(2-methacryloyloxy-ethyl)dimethyl-ammonium bromide, which is a quaternary ammonium dimethacrylate (QADM). Quaternary ammonium methacrylate (QAM), methacryloyloxy-dodecylpridinium bromide (MDPB), and ionic dimethacrylate (IDMA) derivatives that contain quaternary ammoniums groups have good antimicrobial properties.

Dipropyl ethers substituted with a quaternary ammonium and three hydroxyl groups are excellent moisturizers providing humectancy in both high and low relative humidity environments.

Monoether derivatives ordinarily have an alkyl constituent on the quaternized ammonium group including methyl, ethyl, n-propyl, isopropyl or hydroxyethyl and mixtures thereof. Particularly preferred is a trimethyl ammonium group known as a "trimonium" group.

In one aspect, at least one of $R^1$, $R^2$, $R^3$ and/or $R^4$ has at least eight carbon atoms.

In one aspect, the QAC can be substituted with triclosan.

Quaternized phospholipids are diester and triester phosphatides containing fatty acid esters of various degrees of saturation and carbon chain length attached to a quaternized nitrogen linked to the phosphate group. Variations include a modified glycerol backbone with various esterified alkyl groups.

Quaternized fatty acid triethanolamine ester salts, so-called "esterquats", are cationic surfactants which have excellent composition softening properties and high ecotoxicological compatibility.

The esterquats are normally prepared by a two-stage process in which triethanolamine is first partly esterified with fatty acids and the reaction product is then quaternized with methyl chloride or preferably dimethyl sulfate in isopropyl alcohol. Low-viscosity concentrates of the esterquats in isopropyl alcohol with a solid content of up to 85% by weight can be obtained in this way. Isopropyl alcohol can be removed after quaternization and the resulting esterquats are solid, which can contribute to their processability.

Quaternized phosphate esters useful in the present invention have a phosphate ester moiety and a long carbon chain substituent, preferably having a carbonyl moiety, such as an amide moiety. These quaternized phosphate esters demonstrate exceptional compatibility with anionic surfactants when incorporated into a cleanser composition as disclosed herein. It has been theorized, but is not relied upon herein, that these quaternized phosphate esters are sufficiently hydrophilic to provide a composition having the desired degree of stability to resist phase separation and yet are available to deposit on the skin.

Suitable quaternized phospholipids include quaternized ammonium phosphates of the general formula:

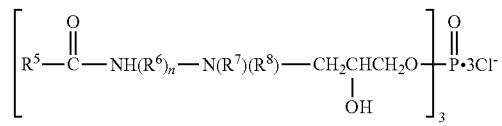

wherein $R^5$ is an alkyl group, more particularly a C1 to a C16 alkyl group;

$R^6$ is an alkylene group, more particularly a C1 to a C10 alkylene, and in one aspect —$CH_2CH_2CH_2$— (a propylene);

$R^7$ and $R^8$, each independently, is an alkyl group, more particularly a C1 to a C10 alkyl group and in one aspect both methyl groups; and n is 1 to about 10, in particular 3.

It should be understood that the halide, Cl could be substituted with any suitable anion(s), such as bromide, methosulfate, ethosulate, etc. and mixtures thereof.

These include, for example:

| INCI Name | FA Source | Primary R-Group | Description |
|---|---|---|---|
| Cocamidopropyl PG-Dimonium Chloride Phosphate | Coconut | Coco | $C_{12}H_{26}O_2$ saturated FA |
| Linoleamidopropyl PG-Dimonium Chloride Phosphate | Safflower | Linoleyl | $C_{18}H_{32}O_2$ unsaturated FA (2 double bonds) |

| INCI Name | FA Source | Primary R-Group | Description |
| --- | --- | --- | --- |
| Sunflowerseedamidopropyl PG-Dimonium Chloride Phosphate | Sunflower | Linoleyl | $C_{18}H_{32}O_2$ unsaturated FA (2 double bonds) |
| Sodium Olivamidopropyl PG-Dimonium Chloride Phosphate | Olive | Oleyl | $C_{18}H_{33}O_2$ unsaturated FA (1 double bond) |
| Stearamidopropyl PG-Dimonium Chloride Phosphate | Palm | Stearyl | $C_{18}H_{36}O_2$ saturated FA |
| Sodium Ricinoleamidopropyl PG-Dimonium Chloride Phosphate | Castor | Ricinoleyl | $C_{18}H_{34}O_3$ unsaturated FA (1 double bond) |
| Dimer Dilinoleamidopropyl PG-Dimonium Chloride Phosphate | Dimer Acid | Dilinoleyl | $C_{36}H_{64}O_4$ unsaturated FA (4 double bonds) |
| Sodium Borageamidopropyl PG-Dimonium Chloride Phosphate | Borage | Linoleyl | $C_{18}H_{32}O_2$ unsaturated FA (2 double bonds) |
| Sodium Grapeseedamidopropyl PG-Dimonium Chloride Phosphate | Grapeseed | Linoleyl | $C_{18}H_{32}O_2$ unsaturated FA (2 double bonds) |
| Myrstamidopropyl PG-Dimonium Chloride Phosphate | Coconut | Myristyl | $C_{14}H_{28}O_2$ saturated FA | or mixtures thereof.

Other suitable quaternized phosphate esters are depicted in general structural formula:

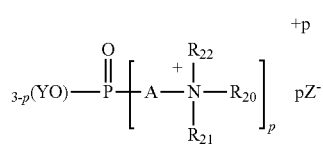

wherein $R_{20}$ is an alkyl chain having 8 to 26 carbon atoms, or $R_{20}$ is an alkamidoalkyl group having the structure

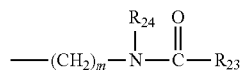

wherein $R_{23}$ is an aryl group, an alkaryl group, a saturated or unsaturated alkyl group, or a saturated or unsaturated hydroxyalkyl group wherein the alkyl or hydroxyalkyl group has about 7 to about 21 carbon atoms; $R_{24}$ is hydrogen, or an alkyl or a hydroxyalkyl group having 1 to about 6 carbon atoms; m is a numeral 1 to about 10; $R_{21}$ and $R_{22}$, independently, are an alkyl or a hydroxyalkyl group having 1 to about 6 carbon atoms; A is a residue of a glycol or a triol having 2 to about 4 carbon atoms, such as, for example, the residue of propylene glycol (i.e., —OCH$_2$CH(OH)CH$_2$— or ethylene glycol —OCH$_2$CH$_2$—); Z is an anion selected from the group consisting of chloride, bromide, methosulfate, ethosulfate, and mixtures thereof; Y is selected from the group consisting of hydrogen, an alkyl group, a hydroxyalkyl group, and an aryl group, either substituted or unsubstituted, wherein the alkyl or the hydroxyalkyl group has 1 to about 22 carbon atoms; and p is a numeral 1 to 3. In one aspect, the quaternized phosphate ester is a quaternized phosphate triester that includes an alkamidopropyl moiety, like stearamidopropyl, as the $R_{20}$ substituent of the compound. For example, the quaternized phosphate ester of general structural formula above that includes an alkamidopropyl moiety as the $R_{25}$ substituent and wherein p is 3.

In addition, alkylhydroxyethyl phosphatidyl PG-imidazolinium chlorides having the structure

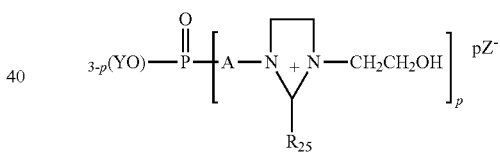

and alkampho phosphatidyl PG-glycinates having the structure

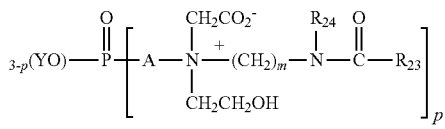

wherein $R_{25}$ is an alkyl group having about 5 to about 21 carbon atoms and all other terms are as defined above, are useful quaternized phosphate esters.

The alkamidopropyl moiety helps the quaternized phosphate ester impart conditioning properties to the skin. An example of an especially useful quaternized phosphate ester is the triester depicted below (X is generally a halide), available commercially under the brand name PHOSPHO-LIPID SV, from Mona Industries, Paterson, N.J., and having the CTFA Dictionary designation of stearamidopropyl phosphatidyl PG-dimonium chloride. This particular compound has p equal to 3 and includes the alkyl moiety of stearic acid as a component of the amido substituent $R_{20}$.

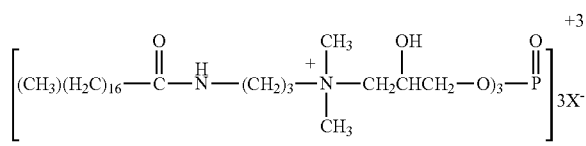

It should be understood that the monophosphate ester (i.e., p=1) and diphosphate ester (i.e., p=2) of the quaternized phosphate esters illustrated above also can be used in the compositions of the present. For example, suitable monophosphate and diphosphate esters of general structural formulae described herein include Y as hydrogen, if the composition pH is sufficiently low such that the acid form of the phosphoric acid ester is present, as opposed to the neutralized, salt form; or Y is an alkyl group, a hydroxyalkyl group, or an aryl group.

Various quaternized phosphate esters are disclosed in Mayhew et al. U.S. Pat. No. 4,209,449, incorporated herein by reference. Other useful quaternized phosphate esters of structural formula (I) are available commercially from Mona Industries, Paterson, N.J., under the PHOSPHOLIPID trade name. Useful commercially available products include, but are not limited to, PHOSPHOLIPID SV, PHOSPHOLIPID EFA, PHOSPHOLIPID CDM, and PHOSPHOLIPID PTC. These compounds have the CTFA designations stearamidopropyl phosphatidyl PG-dimonium chloride, linoleamidopropyl phosphatidyl PG-dimonium chloride, coco phosphatidyl PG-dimonium chloride, and cocamidopropyl phosphatidyl PG-dimonium chloride, respectively. Other useful quaternized phosphate esters are borageamidopropyl phosphatidyl PG-dimonium chloride, laurampho phosphatidyl PG-glycinate, and cocohydroxyethyl phosphatidyl PG-imidazolinium chloride.

Nonionic surfactants include alkyl glucosides or alkanolamides. Suitable alkyl glucosides include, for example, decyl, arachidyl, butyl, C10-16 alkyl, C12-18 alkyl, C12-20 alkyl, caprylyl, caprylyl/capryl, cetearyl, coco, ethyl, hexadecyl D, isostearyl, lauryl, myristyl, octadecyl D, octyldodecyl, undecyl glucosides, or mixtures thereof.

Alkanolamides are the condensation products of a fatty acid, such as those found in soybeans or coconut, oleic acid, etc. and either monoethanolamide or diethanolamine. Suitable alkanolamides include, for example, coconut diethanolamide, coconut diethanolamide (C12-18 cut), soya diethanolamide, coconut monoethanolamide, etc.

Amphoteric surfactants include alkyl amine oxides, such as those depicted by the formula:

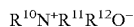

wherein $R^{10}$ is a C1 to a C20 alkyl group; and $R^{11}$ and $R^{12}$, each independently, are C1 to C20 alkyl groups.

In one aspect, $R^{10}$ is a C4 to a C18 alkyl group and $R^{11}$ and $R^{12}$ are both either methyl or ethyl groups.

In another aspect, the alkyl amine oxide is lauryl dimethyl amine oxide or dihydroxyethyl amine oxide.

Suitable nonionic polymers include, for example, hydroxyalkyl guars, alkyl celluloses, hydroxyalkyl alkylcelluloses or polymers containing polyvinylpyrrolidone including polyvinylpyrrolidone itself.

For example, a suitable hydroxyalkyl guar is hydroxylpropyl guar, an alkyl cellulose is methylcellulose, a hydroxyalkyl alkylcellulose is hydroxypropyl methylcellulose, or polyvinylpyrrolidone containing polymer is polyvinylpyrrolidone.

Quaternized polymers include, for example, hydroxyalkyl guar hydroxyalkyltrimonium halides, hydroxyalkyl celluloses, a copolymer of an acrylamide or methacrylamide and a diallyldialkylammonium halide.

For example, a suitable hydroxyalkyl guar hydroxyalkyltrimonium halide is hydroxypropyl guar hydroxypropyltrimonim chloride, hydroxyalkyl cellulose is hydroxyethyl cellulose and a copolymer of acrylamide and diallyldimethylammonium chloride.

Quaternized polymers can comprise monomers of quaternary ammonium metharylate (QAM), methacryloyloxydodecylpridinium bromide (MDPB), and ionic dimethacrylate (IDMA) derivatives.

Skin adjuvants can include one or more of, glycerol esters, silicone derivatives and/or glycols. Suitable examples include polyglyceryl-4 caprate, PEG-7 glyceryl cocoate, glycereth-18 ethylhexanoate and glycereth-18 or methyl gluceth-10 or methyl gluceth-20, dimethicone, PEG-8 dimethicone, a silicone glycol copolymer or cyclomethicone, hexylene glycol or propylene glycol.

The compositions described herein can further include one or more of a urea compound, a chelating agent, an isothaizolinone, an organic acid or the salt of an organic acid, or a halopropynyl alkylcarbamate.

Suitable urea compounds include, for example, imidozlidinyl urea or diazolidinyl urea or mixtures thereof.

Suitable chelating agents include, for example, di- or tetrasodium ETDA, Di- or tetraammonium EDTA or mixtures thereof.

Suitable isothiazolinones include, for example, methyl isothiazolinone or chloromethyl isothiazolinone or mixtures thereof.

Organic acids include, for example citric acid, lactic acid, benzoic acid, sorbic acid, their salts or mixtures thereof.

Halopropynyl alkylcarbamates include, for example, iodopropynyl butylcarbamate, salts or mixtures thereof.

The compositions described herein can further include one or more of a fragrance, a dye, or a pH adjuster.

The antimicrobial compositions described herein do not require a low pH or a high pH to provide a rapid reduction in microbial populations. Antimicrobial preparations of the present invention have a pH of about 5.0 to about 8.0, more particularly of about 5.5 to about 7.0. Within this pH range, the present compositions effectively reduce microbial populations, and are consumer acceptable, i.e., are mild to the skin, are phase stable, and are clear, colorless and provide a desirable moisturizing effect to the skin after the application.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The following paragraphs enumerated consecutively from 1 through 42 provide for various aspects of the present invention. In one embodiment, in a first paragraph (1), the present invention provides a composition comprising: a quaternary ammonium compound; a first surfactant, comprising a quaternized phospholipid; a second surfactant, comprising a nonionic surfactant or amphoteric surfactant; and a nonionic polymer or a quaternized polymer.

2. The composition of paragraph 1, wherein the quaternary ammonium compound of the general formula:

wherein $R^1$, $R^2$, $R^3$ and $R^4$, independently of each other, are alkyl groups, aliphatic groups, aromatic groups, alkoxy groups, polyoxyalkylene groups, alkylamido groups, hydroxyalkyl groups, aryl groups, each with from 1 to 22 carbon atoms or $H^+$ ions; and $X^-$ represents a halogen, acetate, phosphate, nitrate or alkyl sulfate.

3. The composition of paragraph 2, wherein at least one of $R^1$, $R^2$, $R^3$ and/or $R^4$ has at least eight carbon atoms.

4. The composition of paragraph 2, wherein the quaternary ammonium compound is alkyl trimethyl ammonium chloride, alkyl dimethyl benzyl ammonium chloride (ADBAC), alkyl dimethyl ethylbenzyl ammonium chloride, dialkyl dimethyl ammonium chloride, benzethonium chloride, N,N-bis-(3-aminopropyl)dodecylamine, chlorhexidine gluconate, PHMB (polyhexamethylene biguanide), salt of a biguanide, a substituted biguanide derivative, an organic salt of a quaternary ammonium containing compound or an inorganic salt of a quaternary ammonium containing compound or mixtures thereof.

5. The composition of any of paragraphs 1 through 4, wherein the quaternized phospholipid is cocamidopropyl PG-dimonium chloride phosphate, linoleamidopropyl PG-dimonium chloride phosphate, stearamidopropyl PG-dimonium chloride phosphate, sunflowerseedamidopropyl PG-dimonium chloride phosphate, sodium olivamidopropyl PG-dimonium chloride phosphate, sodium ricinoleamidopropyl PG-dimonium chloride phosphate, dimer dilinoleamidopropyl PG-dimonium chloride phosphate, sodium borageamidopropyl PG-dimonium chloride phosphate, sodium grapeseedamidopropyl PG-dimonium chloride phosphate, myrstamidopropyl PG-dimonium chloride phosphate or mixtures thereof.

6. The composition of any of paragraphs 1 through 5, wherein the nonionic surfactant is an alkyl glucoside.

7. The composition of paragraph 6, wherein the alkyl glucoside is decyl, arachidyl, butyl, C10-16 alkyl, C12-18 alkyl, C12-20 alkyl, caprylyl, caprylyl/capryl, cetearyl, coco, ethyl, hexadecyl D, isostearyl, lauryl, myristyl, octadecyl D, octyldodecyl, undecyl glucoside or mixtures thereof.

8. The composition of any of paragraphs 1 through 5, wherein the nonionic surfactant is an alkanolamide.

9. The composition of paragraph 8, wherein the alkanolamide is coconut diethanolamide, coconut diethanolamide (C12-18 cut), soya diethanolamide, coconut monoethanolamide or mixtures thereof.

10. The composition of any of paragraphs 1 through 5, wherein the amphoteric surfactant is an alkyl amine oxide.

11. The composition of paragraph 10, wherein the alkyl amine oxide has the formula:

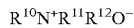

wherein $R^{10}$ is a C1 to a C20 alkyl group; and
$R^{11}$ and $R^{12}$, each independently, are C1 to C20 alkyl groups.

12. The composition of paragraph 11, wherein $R^{10}$ is a C4 to a C18 alkyl group and $R^{11}$ and $R^{12}$ are both either methyl or ethyl groups.

13. The composition of paragraph 10, wherein the alkyl amine oxide is lauryl dimethyl amine oxide or dihydroxyethyl amine oxide.

14. The composition of any of paragraphs 1 through 13, wherein the nonionic polymer is a hydroxyalkyl guar, an alkyl cellulose, a hydroxyalkyl alkylcellulose or a polymer containing polyvinylpyrrolidone.

15. The composition of paragraph 14, wherein the hydroxyalkyl guar is hydroxylpropyl guar.

16. The composition of paragraph 14, wherein the alkyl cellulose is methylcellulose.

17. The composition of paragraph 14, wherein the hydroxyalkyl alkylcellulose is hydroxypropyl methylcellulose.

18. The composition of paragraph 14, wherein the polyvinylpyrrolidone containing polymer is polyvinylpyrrolidone.

19. The composition of any of paragraphs 1 through 13, wherein the quaternized polymer is a hydroxyalkyl guar hydroxyalkyltrimonium halide.

20. The composition of paragraph 19, wherein the hydroxyalkyl guar hydroxyalkyltrimonium halide is hydroxypropyl guar hydroxypropyltrimonim chloride.

21. The composition of any of paragraphs 1 through 13, wherein the quaternized polymer is a quaternized hydroxyalkyl cellulose.

22. The composition of paragraph 21, wherein the quaternized hydroxyalkyl cellulose is hydroxyethyl cellulose.

23. The composition of any of paragraphs 1 through 13, wherein the quaternized polymer is a copolymer of an acrylamide or a methacrylamide and a diallyldialkylammonim halide.

24. The composition of paragraph 23, wherein the copolymer is of an acrylamide and a diallyldimethylammonium chloride.

25. The compositions of any of paragraphs 1 through 24, further comprising one or more of a glycerol ester, a silicone derivative or a glycol.

26. The composition of paragraph 25, wherein the glycerol ester is polyglyceryl-4 caprate, PEG-7 glyceryl cocoate, glycereth-18 ethylhexanoate and glycereth-18 or methyl gluceth-10 or methyl gluceth-20.

27. The composition of paragraph 25, wherein the silicone is dimethicone, PEG-8 dimethicone, a silicone glycol copolymer or cyclomethicone.

28. The composition of paragraph 25, wherein the glycol is hexylene glycol or propylene glycol.

29. The composition of any of paragraphs 1 through 28, further comprising one or more of a urea compound, a chelating agent, an isothaizolinone, an organic acid or the salt of an organic acid, or a halopropynyl alkylcarbamate.

30. The composition of paragraph 29, wherein the urea compound is one of imidozlidinyl urea or diazolidinyl urea or mixtures thereof.

31. The composition of paragraph 29, wherein the chelating agent is di- or tetrasodium ETDA, di- or tetraammonium EDTA or mixtures thereof.

32. The composition of paragraph 29, wherein the isothiazolinone is methyl isothiazolinone or chloromethyl isothiazolinone or mixtures thereof.

33. The composition of paragraph 29, wherein the organic acid is citric acid, lactic acid, benzoic acid, sorbic acid, their salts or mixtures thereof.

34. The composition of paragraph 29, wherein the halopropynyl alkylcarbamate is iodopropynyl butylcarbamate, its salts or mixtures thereof.

35. The composition of any of paragraphs 1 through 34, further comprising a fragrance.
36. The composition of any of paragraphs 1 through 35, further comprising a dye.
37. The composition of any of paragraphs 1 through 36, further comprising a pH adjuster.
38. The composition of any of paragraphs 1 through 37, wherein the composition is clear.
39. The composition of any of paragraphs 1 through 28, wherein the composition is stable at 40° C., 75% relative humidity for 180 or 6 months days.
40. The composition of any of paragraphs 1 through 39, wherein the composition is prepared at ambient conditions, not requiring heating during the preparation process.
41. The composition of any of paragraphs 1 through 41, wherein the composition has an $ET_{50}$ value of 4 or greater.
42. The composition of paragraph 41, wherein the $ET_{50}$ value is greater than 12.
43. The composition of paragraph 41, wherein the $ET_{50}$ value is greater than 13.

The embodiments will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Mixing Procedure

Compositions 1-11

1. Charge mixing vessel with formulation water, start heating to 35° C. Start propeller at ~300 rpm.
2. Add quaternized polymer as water reaches ~25-27° C. Continue mixing until solution is clear, and without "fish eyes", about 3 minutes.
3. Add active and Na$_2$EDTA. Mix until solution is clear & homogenous, about 90 seconds.
4. Add surfactants. Mix until solution is clear & homogenous, about 4 minutes.
5. Add skin adjuvants. Mix until solution is clear & homogenous (90 sec.), then remove from heat.
6. Add preservatives. Mix until solution is clear & homogenous, about 2 minutes.
7. Add fragrance. Mix until solution is clear & homogenous, about 2 minutes.
8. pH adjust as necessary.
9. Continue mixing for 30 minutes to ensure a homogenous, stable solution.

Mixing Procedure

Compositions 12-13

1. Charge mixing vessel with formulation water. Start propeller at ~300 rpm.
2. Add quaternized polymer and mix until fully dispersed (30 sec.), then add 0.02% citric acid. Continue mixing until polymer is fully hydrated and solution is clear & colorless, about 1 minute.
3. Add active and Na$_2$EDTA. Mix until solution is clear & homogenous, about 2 minutes.
4. Add surfactants. Mix until solution is clear & homogenous, about 4 minutes.
5. Add skin adjuvants. Mix until solution is clear & homogenous, about 90 seconds.
6. Add preservatives. Mix until solution is clear & homogenous, about 2 minutes.
7. Add fragrance. Mix until solution is clear & homogenous, about 2 minutes.
8. pH adjust as necessary.
9. Continue mixing for 30 minutes to ensure a homogenous, stable solution.

Samples 12 and 13, in particular, are "cold processed". That is no heating of the solutions was required to prepare the compositions. That provides a cost savings in terms of not requiring heating of a commercial sized reactor to prepare the compositions among other attributes. Advantageously, the polymer is hydrated by slightly acidifying the solution and the remaining components are essentially water soluble.

Urea used in the formulations acts as a humectant. It is hydroscopic and will bind water and hold it to the skin when ambient humidity is high. A minimal amount was selected so not to attract water from deeper layers of the skin in low ambient humidity conditions, which isn't desirable.

| Component | 1 (% w/w) | 2 (% w/w) | 3 (% w/w) | 4 (% w/w) | 5 (% w/w) | 6 (% w/w) | 7 (% w/w) |
|---|---|---|---|---|---|---|---|
| Active | | | | | | | |
| Benzethonium Chloride | 0.1 | 0.1 | 0.1 | 0.1 | 0.1 | 0.1 | 0.1 |
| Surfactants | | | | | | | |
| CAP PG Dimonium Chloride Phosphate | 1.0 | 1.0 | 1.0 | 1.0 | 1.0 | 1.0 | 1.0 |
| Lauryl Dimethyl Amine Oxide | | | | | | | |
| Lauryl Glucoside | 0.3 | 0.3 | 0.3 | 0.3 | 0.3 | 0.4 | 0.5 |
| Decyl Glucoside | | | | | | | |
| Polymers | | | | | | | |
| Hydroxypropyl Guar (Jaguar HP120/Rhodia) | 0.1 | 0.1 | 0.1 | 0.1 | 0.1 | 0.1 | 0.1 |
| Hydroxypropyl Guar Hydroxypropyltrimonium Chloride (Jaguar C-162) | | | | | | | |
| Skin Adjuvants | | | | | | | |
| Glycerin | | | 0.3 | 0.2 | 0.2 | | |
| Urea | | 0.2 | 0.2 | 0.2 | 0.2 | | 0.2 |

-continued

| Component | | | | | | | |
|---|---|---|---|---|---|---|---|
| Polyglyceryl-4 Caprate (Tegosoft PC 41/Evonik) | | | | | | 0.4 | 0.3 |
| PEG-7 Glyceryl Cocoate | | | | | | | |
| Glycereth-18 Ethylhexanoate (and) Glycereth-18 (Hest G-18-O/Global Seven) | | | | | 0.2 | | |
| Propylene Glycol | | | | | | | |
| Dimethicone | | | | 0.1 | | | |
| Preservatives | | | | | | | |
| Imidozlidinyl Urea | | | | | | | |
| Disodium EDTA | | | | | | | |
| Fragrance | | | | | | | |
| FL-1227 W/S1 | | | | | | | |
| pH Adjustment | | | | | | | |
| Lactic Acid (50% w/w) | 0.1 | 0.1 | 0.1 | | | | |
| Citric Acid (50% w/w) | | | | | | | |
| Solvent | | | | | | | |
| DI Water | 98.4 | 98.2 | 97.9 | 98.0 | 97.9 | 98.0 | 97.8 |
| Total | 100.0 | 100.0 | 100.0 | 100.0 | 100.0 | 100.0 | 100.0 |

| Component | 8 (% w/w) | 9 (% w/w) | 10 (% w/w) | 11 (% w/w) | 12 (% w/w) | 13 (% w/w) |
|---|---|---|---|---|---|---|
| Active | | | | | | |
| Benzethonium Chloride | 0.1 | 0.1 | 0.1 | 0.1 | 0.1 | 0.1 |
| Surfactants | | | | | | |
| CAP PG Dimonium Chloride Phosphate | 1.1 | 1.0 | 1.0 | 1.0 | 1.0 | 1.0 |
| Lauryl Dimethyl Amine Oxide | | | | | 0.5 | |
| Lauryl Glucoside | 0.2 | 0.3 | 0.3 | 0.3 | | 0.3 |
| Decyl Glucoside | | | | | | |
| Polymers | | | | | | |
| Hydroxypropyl Guar (Jaguar HP120/Rhodia) | 0.1 | 0.1 | 0.1 | 0.1 | | |
| Hydroxypropyl Guar Hydroxypropyltrimonium Chloride (Jaguar C-162) | | | | | 0.1 | 0.1 |
| Skin Adjuvants | | | | | | |
| Glycerin | | | | | | |
| Urea | 0.2 | 0.2 | 0.2 | 0.2 | 0.2 | 0.2 |
| Polyglyceryl-4 Caprate (Tegosoft PC 41/Evonik) | 0.4 | 0.3 | 0.4 | 0.3 | | 0.3 |
| PEG-7 Glyceryl Cocoate | | | | | 0.2 | |
| Glycereth-18 Ethylhexanoate (and) Glycereth-18 (Hest G-18-O/Global Seven) | 0.2 | 0.2 | 0.2 | 0.2 | 0.2 | 0.2 |
| Propylene Glycol | | | | | | |
| Dimethicone | | | | | | |
| Preservatives | | | | | | |
| Imidozlidinyl Urea | | | 0.3 | 0.3 | 0.3 | 0.3 |
| Disodium EDTA | | 0.1 | 0.1 | 0.1 | 0.1 | 0.1 |
| Fragrance | | | | | | |
| FL-1227 W/S1 | | | | 0.1 | 0.1 | 0.1 |
| pH Adjustment | | | | | | |
| Lactic Acid (50% w/w) | | | | | | |
| Citric Acid (50% w/w) | | | | | 0.1 | 0.1 |

-continued

| | | | | | | |
|---|---|---|---|---|---|---|
| Solvent | | | | | | |
| DI Water | 97.7 | 97.7 | 97.3 | 97.3 | 97.1 | 97.2 |
| Total | 100.0 | 100.0 | 100.0 | 100.0 | 100.0 | 100.0 |

| Composition | Note |
|---|---|
| 1 | Transient Stickiness during dry-down. After completely dry, feels very smooth on skin. Not tacky at all. Slight haze from guar derivative. |
| 2 | Addition of urea does not add to stickiness during dry-down phase. Increased moisture retention from composition 1. Slight haze from guar derivative. |
| 3 | Feeling of tackiness was more persistent in both dry-down and after dry. Moisture retention is improved from compositions 1 & 2. Slight haze from guar derivative. |
| 4 | Not soluble in this surfactant package. Forms oil pockets. |
| 5 | Hazes out. |
| 6 | Really nice after-feel with short dry-down phase. Very little tackiness after dry-down. Slight haze from guar derivative. |
| 7 | Increased moisture retention from composition 6. Very nice after feel. Slight haze from guar derivative. |
| 8 | Best embodiment so far, with great moisture retention, and little to no tackiness during dry-down. Relatively short dry-down phase. Slight haze from guar derivative. |
| 9 | Best embodiment so far, with great moisture retention, and little to no tackiness during dry-down. |
| 10 | No change in aesthetic properties or solubility from composition 8. Slight haze from guar derivative. |
| 11 | No change in aesthetic properties or solubility from composition 8. Slight haze from guar derivative. |
| 12 | Changed secondary surfactant from Lauryl Glucoside to Lauryl Dimethyl Amine Oxide. Increase in foam volume with larger, fluffier bubbles observed. Also switched guar derivatives (to Jag C-162), and saw clear colorless solution. PEG-7 Glyceryl Cocoate adds a nice after-feel and is a second option to replace Polyglyceryl-4 Caprate. |
| 13 | Jaguar C-162 clears the haze seen in the full formula (comp. 11). |

Jaguar is the trade name used by the supplier Rhodia.

Tegosoft PC-41/Evonik is the trade name and supplier for this product.

Hest G-18-O/Global Seven is the trade name and supplier for this product.

FL-1227 W/S1 is the fragrance used. It is recognized as "Fragrance" by the international community.

CAP PG Dimonium chloride phosphate was selected in place of surfactants like cocamidopropyl betaine (CAPB) or sodium lauryl ether sulfate (SLES). CAPB is frequently used in "mild" personal care formulations because it is more mild than SLS or SLES as a primary surfactant. However, CAPB is detrimental to the antimicrobial efficacy of the product. The CAP PG-dimonium chloride phosphate alleviates the disadvantages of CAPB and is also helpful in that it mitigates the irritation caused by other, secondary surfactants which CAPB cannot do.

Antimicrobial Efficacy

Antimicrobial efficacy was performed by MicroBioTest, Sterling, Va. The tests were performed per the protocol listed in the first aid antiseptic FDA monograph. The monograph reference is: US 21 CFR Part 333 and 369. The subsection that deals with testing antimicrobial efficacy is part 333.70 (pg. 33678-33680). The general take-away from this section is that compliance is characterized as >3 $\log_{10}$ reduction within 10 minutes at 32° C. in the presence of 10% serum in vitro. Challenge organisms are listed in the table below:

| Name | ATCC No. |
|---|---|
| Staphylococcus aureus | 6538 |
| Escherichia Coli | 8739 |
| Pseudomonas aeruginosa | 9027 |

Sample 12 was tested against these organisms using the procedure outlined in the FDA antiseptic monograph. The following results were obtained:

| Name | ATCC No. | $\log_{10}$ reduction |
|---|---|---|
| Staphylococcus aureus | 6538 | >7.82 |
| Escherichia Coli | 8739 | >8.34 |
| Pseudomonas aeruginosa | 9027 | >7.83 |

Sample 12 was also tested against 13 additional organisms that are of concern to those in the medical field. The protocol used to test these 13 additional organisms differed from the monograph test in that 10% serum was not added and the test was conducted at 5 minutes instead of 10. The results are provided below:

| Name | ATCC No. | $\log_{10}$ reduction |
|---|---|---|
| Acinetobacter baumannii | 19606 | >6.16 |
| Candida albicans | 10231 | >5.09 |
| Enterobacter aerogenes | 10348 | >6.58 |
| Vancomycin Resistant Enterococcus faecalis (VRE) | 51299 | >6.12 |
| Enterococcus faecium | 51299 | >5.76 |
| Escherichia coli (E. coli O:157) | 11229 | >6.31 |
| Klebsiella pneumoniae | 10031 | >6.03 |
| Proteus mirabilis | 7002 | 4.95 |
| Pseudomonas aeruginosa (Resistant Strain) | 15442 | >6.25 |
| Serratia marcescens | 14756 | 3.28 |
| Methicillin Resistant Staphylococcus aureus (MRSA) | 33591 | >6.34 |
| Staphylococcus epidermidis | 12228 | >6.25 |

| Name | ATCC No. | $Log_{10}$ reduction |
|---|---|---|
| Steptococcus pneumoniae | 6305 | >6.26 |

Irritancy

Example 1

In vitro irritancy was tested using a commercially available kit "EpiDerm MTT ET50 Protocol (EPI-200)", available from MatTek Corporation (Ashland, Mass.). The test kit is used as a validated replacement for in vivo irritation testing otherwise known as "Draize testing", in the EU (OECD TG439). Our method of data analysis and outcome prediction is altered slightly to determine relative differences in irritation potential between experimental neat materials tested within the same kit.

The test consists of a topical exposure of the neat experimental material to a reconstructed human epidermis (RhE) model followed by a cell viability assay. The cell viability test method is based on the enzymatic conversion of mitochondrial dehydrogenase with MTT [(3-4,5-dimethyl thiazole-2-yl) 2,5-diphenyltetrazolium bromide], resulting in a blue formazan salt, which is than extracted from the tissues and quantitated. The reduction in the concentration of the formazan salt in tissues exposed to experimental materials is compared to the concentration in tissues exposed to a negative control, phosphate buffered saline (PBS), to calculate relative % cell viability. This data is further reduced to an $ET_{50}$ value, or an estimated time for the RhE model to be exposed to the experimental test material to reduce cell viability to 50%.

EpiDerm tissues are conditioned overnight at 37±2° C., 5% $CO_2$, to relieve stress from the shipping process. After this initial incubation, assay culture medium is exchanged and three tissues per sample (experimental material, negative and positive controls) are treated and held for one of three time points (1, 4 or 24 hrs). This gives a total of one tissue per time point, for each sample. After the appropriate amount of incubation time has passed, each tissue is rinsed with PBS to completely remove the sample and is then exposed to an appropriate amount of MTT (1 mg/mL) and incubated for 3 hours. After the three hour incubation in MTT, the formazan salt is extracted using 2.0 mL of isopropanol and the optical density (OD) of each sample is measured at 570 nm. Relative cell viability is calculated as a % of the mean of the negative control tissue. Dose-response curves are constructed for each sample and an $ET_{50}$ value is calculated. These $ET_{50}$ values are compared to $ET_{50}$ values of known irritants and non-irritants to determine the relative irritancy of the experimental materials.

| Sample | Chemistry | $ET_{50}$ Value | $R^2$ | Expected In vivo Irritancy Score |
|---|---|---|---|---|
| | Composition 12 | 14.388 | 0.9586 | very mild |
| | Commercially Available No-Rinse Antimicrobial Cleanser | 2.515 | 1.000 | moderate |
| Positive Control | 1.0% Triton X-100 | 12.69 | 0.945 | very mild |

| Irritancy Scale | | |
|---|---|---|
| $ET_{50}$ | Expected In vivo Irritancy | Example |
| <0.5 | strong/severe, possible corrosive concentration | Nitric Acid |
| 0.5-4 | moderate | 1% SDS |
| 4-12 | moderate to mild | 1% Triton X-100 |
| 12-24 | very mild | Baby Shampoo |
| ≥24 | Non-irritating | 10% Tween 20 |

Example 2

Skin irritation properties of the combination of specific materials included in the new experimental Sample 6, as well as the irritation properties of competitor products were tested. Formulation is centred around two main objectives, i) development of chemistry with improved time kill (TK) efficacy against the FDA monograph organisms (S. aureus and E. coli) and, ii) development of chemistry with improved aesthetics (i.e. lessen the tacky after-feel on the skin after use).

The EpiDerm skin irritation test method is used to quantitate the irritation potential of the experimental chemistry. It is based on a MTT cell viability test method which quantitates the conversion of MTT [(3-4,5-dimethyl thiazole 2-yl) 2,5-diphenyltetrazoliumbromide] to a blue formazan salt. The conversion of MTT to a blue formazan salt occurs when active dehydrogenase enzyme cleaves the tetrazolium ring present in MTT. Active dehydrogenase enzymes are only found in mitochondria in viable cells. This colorimetric change is measured on a 96-well microtiter plate at 570 and 650 nm, with the latter being subtracted from the former to eliminate background noise. The data from the TA treated tissue is then compared to data from the negative control (buffered saline) treated tissue to determine cell viability, and consequently skin irritation potential.

Samples Tested:
Test Article Formulation Summary.

| Sample # | Chemistry |
|---|---|
| 1 | QAC + Amine Oxide |
| 2 | QAC + Amine Oxide + Cocamidopropyl Betaine |
| 3 | QAC + Amine Oxide + CAP PG-Dimonium Chloride Phosphate |
| 4 | Covidien Kendall Antimicrobial Cleanser (lot #: 30721) |
| 5 | Medline Remedy Antimicrobial Cleanser (lot #: 2J8798) |
| 6 | Sample 6 (lot #: 12052012B) |
| 7 | QAC + Amine Oxide + Quaternium-52 |
| Negative Control | DPBS |

QAC is benzethonium chloride.
Amine Oxide is lauryl dimethyl amine oxide.
DPBS Dulbecco's phosphate buffered saline.
Covidien Kendal Antimicrobial Cleanser components: Active: benzalkonium chloride 0.13%; Inactives: water, polysorbate 20, linoleamidopropyl PG-dimonium chloride phosphate, propylene glycol, citrus aurantium bergamia (bergamot) fruit oil, citrus medica vulgaris peel oil, retinyl palmiate, tocopheryl acetate, methylparaben, propylparaben, diazolidinly urea.
Medline Remedy Antimicrobial Cleanser components: Active: benzalkonium chloride 0.12%; Inactives: aloe barbadensis leaf juice, citrus aurantium dulcis peel oil, citrus grandis peel oil, citrus tangerine peel oil, diazoldinyl urea, glycerin, glycine, hydroxytyrosol, L-proline, L-taurine, methylparaben, methylsulfonylmethane, N-acetyl-L-cysteine, niacinamide, polysorbate 20, propylene glycol, propylparaben, pyridoxine HCl, tetrasodium EDTA, vanillin, water.

| Component | Sample 1 Ideal (% active) | Sample 1 Actual (g) | Sample 2 Ideal (% active) | Sample 2 Actual (g) | Sample 3 Ideal (% active) | Sample 3 Actual (g) |
|---|---|---|---|---|---|---|
| Water | 99.4 | 98.23 | 98.2 | 94.24 | 98.20 | 95.56 |
| Benzethonium Chloride | 0.10 | 0.11 | 0.10 | 0.10 | 0.10 | 0.10 |
| Lauryl Dimethyl Amine Oxide | 0.5 | 1.68 | 0.5 | 1.69 | 0.5 | 1.66 |
| Cocamidopropyl PG-Dimonium Chloride Phosphate | 0 | 0 | 0 | 0 | 1.20 | 2.69 |
| Total | 100.00 | 100.02 | 100.00 | 100.08 | 100.00 | 100.01 |

| Component | Sample 7 Ideal % active (actual g) |
|---|---|
| Water | 98.2; 97.02 |
| Benzethonium Chloride | 0.10 |
| Lauryl Dimethylamine oxide | 0.50; 1.68 |
| Quaternium 52 | 1.20 |
| Total | 100.00 |

*** Lauryl Dimethylamine oxide is a 30% active/70% water mixture. This is why "ideal" and "actual" are noted.

All samples prepared by adding all ingredients to water and mixing with propeller agitator for 10 minutes.

Sample 6 was prepared with:

| Component | Ideal wt % | Actual (g) | Actual (% w/w) |
|---|---|---|---|
| Hydroxypropyl Guar | 0.1 | 5.49 | 0.10 |
| Imidazolidinyl Urea | 0.3 | 16.52 | 0.30 |
| Disodium EDTA | 0.10 | 5.48 | 0.10 |
| Benzethonium Chloride | 0.10 | 6.0 | 0.10 |
| Urea | 0.20 | 11.02 | 0.2 |
| Cocamidopropyl PG Dimonium Chloride Phosphate | 1.00 | 55.04 | 1.00 |
| Lauryl Dimethyl Amine Oxide | 0.50 | 27.54 | 0.50 |
| PEG-7 Glyceryl Cocoate | 0.20 | 11.02 | 0.20 |
| Hest G-18-O | 0.20 | 11.79 | 0.21 |
| Purified Water | 97.17 | 5344.5 | 97.15 |
| FL-1227 W/S1 118537 | 0.13 | 7.32 | 0.13 |
| Lactic Acid | 0.002 | 0.11 | 0.00 |
| Total | 100.00 | 5501.33 | 100.00 |

The preparation procedure for Sample 6 was as follows. Purified water was charged into a stainless steel vessel. Hydroxypropyl guar was added and the mixture/solution was agitated for about 5 minutes to provide an even dispersion. Lactic acid was then added and the mixture was stirred for about 10 minutes. Disodium EDTA, benzethonium chloride and urea were added, with stirring, until the solution was clear and homogenous. To this was added cocamidopropyl PG dimonium chloride phosphate. The mixture was stirred for about 5 minutes to allow for complete incorporation. Lauryl dimethyl amine oxide was then added and stirred for about 5 minutes. PEG-7 glyceryl cocoate and Hest G-18-0 were then added slowly and after addition was completed, the solution was stirred for an additional 10 minutes providing a clear homogenous solution. To this was added the fragrance and the solution was stirred for about 5 minutes before the pH was adjusted with lactic acid. A pH of 5.67 was provided. The final mixture was stirred for an additional 30 minutes. The preparation was all performed at room temperature.

Test Materials:

EpiDerm™ Skin Model (EPI-200) in conjunction with MTT Effective Time-50 Protocol, MatTek Corporation, Ashland, Mass.; DPBS solution used as provide in EpiDerm kit.

Quantikine ELISA Human CXCL8/IL-8, R&D Systems, Minneapolis, Minn.

Quantikine ELISA Human IL-1α/IL-1F1, R&D Systems, Minneapolis, Minn.

Thermo Scientific Multiskan Spectrum (v1.2) running on SkanIt Software (v2.4.4 RE)

Testing Procedure:

EpiDerm Skin Irritation Test

Day 0:

1. Reconstituted human epithelial cells by equilibration (37±2° C., 5% $CO_2$) overnight.

Day 1-3:

1. Treat cells with 100 μl of appropriate test article.
2. After allotted exposure time (e.g. 1, 4 and 24 hrs.) rinse cells with phosphate buffered saline (PBS).
3. Remove excess PBS using sterile cotton tipped swabs.
4. Expose cells to MTT solution. MTT solution is converted to a blue formazan salt by a mitochondrial dehydrogenase found in viable cells.
5. After exactly 3 hours, remove cells from MTT solution and residual MTT is removed using sterile cotton tipped swabs before exposure to 2.00 mL of isopropyl alcohol (IPA). IPA solubilizes the blue formazan salt produced in step 4, forming a homogenous solution appropriate for measuring optical density (OD).
6. Analyze sample by MultiSkan multiwell spectrophotometer at 570 nm and 630 nm calibrated against a 200 μl IPA aliquot blank.

Analysis:

EpiDerm Skin Irritation Test

Average absorbance values obtained from the multiwell spectrophotometer are manipulated to produce a percent viability value which is plotted against exposure time (hrs.) on a semi-log scale. A skin irritancy value ($ET_{50}$ value) is determined by adding a linear trendline and using the resulting equation to calculate the number of hours to reach fifty percent cell viability.

The dose-response curve for Sample 1 is depicted in FIG. 1. Panel A shows an $R^2$ value of 0.3829. The calculated $ET_{50}$ value for this sample using the trendline shown in panel A is 7.44. Panel B shows the same data with the last time point omitted. The calculated $ET_{50}$ value for the trendline depicted in panel B is 2.83.

The dose-response curve for Sample 2 is depicted in FIG. 2. Panel A shows an $R^2$ value of 0.6426. The calculated $ET_{50}$ value for this sample using the trendline shown in panel A is 10.06. Panel B shows the same data with the last time point omitted. The calculated $ET_{50}$ value for the trendline depicted in panel B is 3.46.

The dose-response curve for Sample 3 is depicted in FIG. 3. Panel A shows an $R^2$ value of 0.5986. The calculated $ET_{50}$ value for this sample using the trendline shown in panel A is 9.63. Panel B shows the same data with the last time point omitted. The calculated $ET_{50}$ value for the trendline depicted in panel B is 3.33.

The dose-response curve for Sample 7 is depicted in FIG. 4. Panel A shows an $R^2$ value of 0.4610. The calculated $ET_{50}$ value for this sample using the trendline shown in panel A is 6.53. Panel B shows the same data with the last time point omitted. The calculated $ET_{50}$ value for the trendline depicted in panel B is 2.81.

The dose-response curve of Sample 4 depicted in FIG. 5 shows excellent linearity as shown by an $R^2$ value of 0.9992. The $ET_{50}$ value for this sample was 15.19, which falls under the very mild clinical rating.

The dose-response curve of Sample 5 is depicted in FIG. 6 shows good linearity as shown by an $R^2$ value of 0.9876. The $ET_{50}$ value for this sample was 15.91, which falls under the very mild clinical rating.

The dose-response curve for Sample 6 depicted in FIG. 7 shows good linearity as shown by an $R^2$ value of 0.9684. The $ET_{50}$ value for this sample was 13.69, which falls under the very mild clinical rating.

EpiDerm MTT ET50 test results are shown below. An $R^2$ value of >0.70 is considered acceptable for a biological test system. Where an $R^2$ value of >0.70 was not achieved, adjusted $ET_{50}$ values are given.

| Sample # | $ET_{50}$ Value | $R^2$ | Expected In vivo Irritancy Score | Adjusted $ET_{50}$ Value | $R^2$ | Expected In vivo Irritancy Score |
|---|---|---|---|---|---|---|
| 1 | 7.438 | 0.3829 | very mild | 2.834 | 1.000 | Moderate |
| 2 | 10.060 | 0.6426 | very mild | 3.464 | 1.000 | Moderate |
| 3 | 9.629 | 0.5986 | very mild | 3.325 | 1.000 | Moderate |
| 7 | 6.526 | 0.4610 | very mild | 2.811 | 1.000 | Moderate |
| 4 | 15.193 | 0.9992 | very mild | — | — | — |
| 5 | 15.911 | 0.9867 | moderate | — | — | — |
| 6 | 13.688 | 0.9684 | very mild | — | — | — |

Samples 1 through 3 and 7 are mixtures of select ingredients and the data generated from these samples support the efficacy of Sample 6. For example, Sample 1 consists of irritating quaternary ammonium compound (QAC) and amine oxide that are also present in Sample 6 Sample 1 shows an $ET_{50}$ value that is very poor and the clinical rating is assigned as "moderate". The addition of mild surfactants to an anionic surfactant system reduces the irritancy potential beyond what is expected by simple additive rules. The mechanism for this phenomenon can be attributed to the lowering of the critical micelle concentration in the resulting mixed micelle. Also, the milder surfactant may compete with the harsher one for binding sites on the stratum corneum.

The data collected shows that adding a betaine or a phospholipid surfactant to the primary irritants can decrease the total irritation potential of the composition. The addition of a betaine-based surfactant to a QAC active antimicrobial may reduce the antimicrobial efficacy of the product. However, the addition of a phospholipid surfactant to a QAC active antimicrobial has little effect on the antimicrobial efficacy. Phospholipid based surfactants show the same ability to reduce irritation potential while not affecting the antimicrobial efficacy of the product. This type of reduction in irritation potential has not been observed with the addition of other types of commonly used quaternized compounds, including quaternium-52.

Samples 4 through 6 as tested were complete formulas: two commercial samples and the Sample 6 cleanser. The commercial samples show very low irritation potential which is can be attributed to the use of very mild surfactants such as polysorbate-20. However, the addition of this particular surfactant results in a decreased antimicrobial product.

Cleanser Skin Feel Survey

A small consumer panel was conducted using the following steps:

Cleanse hands with gel-liquid cleanser provided by survey administrator. Rinse and dry hands thoroughly.

Apply 1.0 mL of first sample to the hands. Rub sample into the skin, including: palms, back of hand, and fingers. To allow for skin to dry completely, wait for 60 seconds after application to rate skin feel property.

Indicate on a scale of 0-5 the degree of tackiness felt after the sample is completely dry. The scale is as follows: 0 is no tackiness, 5 is extremely tacky.

Rinse residual product off of hands, cleanse with gel-liquid cleanser provided by survey administrator, rinse and dry thoroughly.

Repeat steps 2-4 for each sample tested.

Because post-use skin feel is a desirable aesthetic feature of all no-rinse cleansers, the lower the tackiness rating, the more advantageous the formula in a consumer market. As shown in FIG. 8, the commercially available no-rinse antimicrobial formula had an average score of 4.0, and DI Lab water had an average score of 0.7. The two experimental formulas fell between these two values with averages ranging from 1.7-2.3. This distribution shows that all experimental formulas leave a less tacky residue after drying on the hands than the commercially available no-rinse antimicrobial formula. An arbitrary 5% error was calculated to assess the validity of the results.

| | Sample | | |
|---|---|---|---|
| Volunteer | Water | Composition 12 | Composition 13 | Commercially Available No-Rinse Antimicrobial Cleanser |
| 1 | 0.00 | 1.50 | 2.00 | 4.00 |
| 2 | 0.00 | 0.00 | 0.00 | 4.00 |
| 3 | 0.90 | 2.20 | 3.10 | 4.90 |
| 4 | 2.00 | 4.00 | 5.00 | 4.00 |

-continued

| | Sample | | | |
|---|---|---|---|---|
| Volunteer | Water | Composition 12 | Composition 13 | Commercially Available No-Rinse Antimicrobial Cleanser |
| 5 | 2.00 | 3.00 | 4.00 | 5.00 |
| 6 | 0.00 | 1.10 | 2.10 | 4.90 |
| 7 | 0.00 | 0.00 | 0.00 | 1.00 |
| Average | 0.70 | 1.69 | 2.31 | 3.97 |
| 5% Error | 0.035 | 0.08 | 0.12 | 0.20 |

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. An antimicrobial composition for use in dermal cleansing comprising an effective amount of:
    benzethonium chloride;
    a first surfactant comprising a quaternized phospholipid, wherein the quaternized phospholipid is a cocamidopropyl PG-dimonium chloride phosphate;
    a second surfactant comprising lauryl dimethyl amine oxide;
    PEG-7 glyceryl cocoate and glycereth-18 ethylhexanoate; and
    a quaternized polymer comprising a hydroxypropyl guar hydroxypropyltrimonium chloride;
    wherein the composition has an $ET_{50}$ value of 4 or greater.

2. The compositions of claim 1, further comprising one or more of a silicone skin adjuvant or a glycol.

3. The composition of claim 2, wherein the silicone skin adjuvant is dimethicone, PEG-8 dimethicone, a silicone glycol copolymer or cyclomethicone.

4. The composition of claim 2, wherein the glycol is hexylene glycol or propylene glycol.

5. The composition of claim 1, wherein the composition is clear.

6. The composition of claim 1, wherein the composition is phase stable at 40° C., 75% relative humidity for 6 months.

7. The composition of claim 1, further comprising one or more of a urea, a chelating agent, an isothiazolinone, an organic acid or the salt of an organic acid, or a halopropynyl alkylcarbamate.

8. The composition of claim 7, wherein the urea comprises imidazolidinyl urea or diazolidinyl urea or mixtures thereof.

9. The composition of claim 7, wherein the chelating agent comprises di- or tetrasodium EDTA, di- or tetraammonium EDTA or mixtures thereof.

10. The composition of claim 7, wherein the isothiazolinone comprises methyl isothiazolinone or chloromethyl isothiazolinone or mixtures thereof.

11. The composition of claim 7, wherein the organic acid comprises citric acid, lactic acid, benzoic acid, sorbic acid, their salts or mixtures thereof.

12. The composition of claim 7, wherein the halopropynyl alkylcarbamate comprises iodopropynyl butylcarbamate, its salts or mixtures thereof.

13. The composition of claim 1, wherein the weight percent of the benzethonium chloride is 0.1%; wherein the weight percent of the first surfactant, comprising a quaternized phospholipid, wherein the quaternized phospholipid is a cocamidopropyl PG-dimonium chloride phosphate is 1%; wherein the weight percent of the second surfactant, comprising lauryl dimethylamine oxide, is 0.5%; wherein the weight percent of the PEG-7 glyceryl cocoate and the glycereth-18 ethylhexanoate are each 0.2%; and wherein the weight percent of the quaternized polymer comprising a hydroxypropyl guar hydroxypropyltrimonium chloride is 0.1%.

* * * * *